United States Patent [19]

Takahashi et al.

[11] Patent Number: 4,933,342
[45] Date of Patent: Jun. 12, 1990

[54] QUINOXALINE DERIVATIVES AND ANTIULCER AGENTS

[75] Inventors: Toshihiro Takahashi; Koichiro Hagihara; Koichi Nakamaru; Yoshikuni Suzuki, all of Saitama, Japan

[73] Assignee: Nisshin Flour Milling Co., Ltd., Tokyo, Japan

[21] Appl. No.: 331,514

[22] Filed: Mar. 29, 1989

[30] Foreign Application Priority Data

Apr. 11, 1988 [JP]  Japan .................................. 63-87270

[51] Int. Cl.$^5$ .................. A61K 31/495; C07D 403/04; C07D 403/12
[52] U.S. Cl. ...................................... 514/249; 544/354
[58] Field of Search ........................ 544/354; 514/249

[56] References Cited

FOREIGN PATENT DOCUMENTS 209062 9/1987 Japan .

OTHER PUBLICATIONS

Ota et al., Chemical Abstracts, vol. 108, No. 186590 (1988), Abstract for JP 62/20962, (9/14/87).
Okabe et al., Chemical Abstracts, vol. 110, No. 75559 (1989), Abstract for JP 62/161769, (7/17/87).

Primary Examiner—Mukund J. Shah
Assistant Examiner—E. Bernhardt
Attorney, Agent, or Firm—Abelman Frayne Rezac & Schwab

[57]  ABSTRACT

Quinoxaline derivatives of formula (I) are provided.

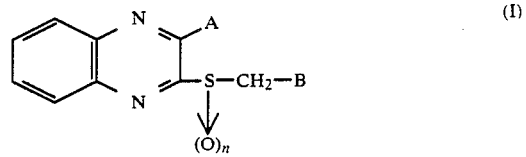

wherein A is a hydrogen atom or 2-quinoxalyl group, B is 2-pyridyl or 4-quinolyl group and n is 0 or 1, or a pharmaceutically acceptable acid addition salt thereof. They are useful as antiulcer agents.

7 Claims, No Drawings

QUINOXALINE DERIVATIVES AND ANTIULCER AGENTS

FIELD OF THE INVENTION

This invention relates to new 2-pyridylmethylsulfinyl- or 4-quinolylmethylsulfinyl-quinoxaline derivatives, or 2-pyridylmethylthio- or 4-quinolylmethylthioquinoxaline derivatives, and pharmaceutically acceptable salts thereof, which are of prominent antiulcer activity.

BACKGROUND OF THE INVENTION

The agents used as the antiulcer drugs include $H_2$-receptor antagonists, anticholinergic agents, gastric mucosal protective agents and antacids, which are used depending upon the symptom of patients. These known agents, however, are of such drawbacks as generally weak activity and frequent occurrence of side effects.

For example, cimetidine, which is a $H_2$-receptor antagonist widely employed, is known to have side effects such as gynecomastism. Moreover, numbers of cases are reported about recurrence of ulcer after suspension of administration with cimetidine. Anticholinergic agents are known to have such side effects as suppression of gastric motility, core-diastasis and thirst. Furthermore, they exhibit activity only for a limited period of time. Antacids are known to have frequent occurrence of such side effects as constipation.

As described above, known antiulcer agents were limitedly used in terms of manner of administration due to their side effects, and they have common drawback of exhibiting somewhat weak activity.

Japanese Patent LOP Publication No. 209062/87 discloses 2-pyridylmethylthio (or sulfinyl) substituted-condensed ring compounds which are useful as the medicine for the prevention and treatment of stomach disorder. In this publication, however, no specific pharmacological data is given on the antiulcer activity.

The present invention results from efforts to develop new quinoxaline derivatives with more improved antiulcer activity.

DISCLOSURE OF THE INVENTION

According to the invention, there are provided quinoxaline compounds of formula (I)

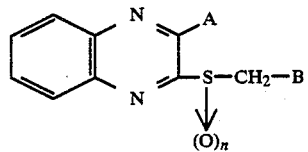

(I)

wherein A is a hydrogen atom or 2-quinoxalyl group, B is 2-pyridyl or 4-quinolyl group and n is 0 or 1, and pharmaceutically acceptable acid addition salts thereof.

The compounds of formula (I) wherein n is 0 are prepared by reacting a compound of formula (II)

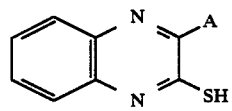

(II)

wherein A has the same meaning as defined above, with a compound of formula (III)

$$HalCH_2\text{-}B \qquad (III)$$

wherein Hal represents a halogen atom and B has the same meaning as defined above in the presence of a base, e.g., inorganic and organic bases, alkali metal alkoxides, or the like. In this reaction, the compound of formula (III) is used in the proportion of 0.5 to 5 moles per mole of the compound (II).

The reaction can be conducted at temperatures between 0° C. and 150° C. in an aqueous medium or an organic solvent, e.g., lower alcohols, ether solvents, ethyl acetate, acetone, halogenated hydrocarbons and the like.

The compounds of formula (III) used in the reaction include those wherein halogen is chlorine, bromine or iodine, but the preferred compounds are those wherein halogen is chlorine because of their easy availability.

Further, the compounds of formula (I) wherein n is 1 are prepared by subjecting the compounds of formula (I) wherein n is 0 to an oxidative reaction.

The oxidizing agents used in the oxidative reaction include peroxides, e.g., peracetic acid, perbenzoic acid, m-chloroperbenzoic acid or hydrogen peroxide, halogen, e.g., bromine, N-bromosuccinimide, nitric acid, chromic acid, potassium permanganate, sodium metaperiodate and the like.

The oxidative reaction is usually carried out using an equal or excess amount of the oxidizing agent for the compound of formula (II).

The reaction may be conducted in an aqueous medium, but is preferably carried out in an organic solvent, e.g., halogenated hydrocarbons such as carbon tetrachloride, dichloromethane, chloroform, etc., or acetic acid. The reaction conditions such as reaction temperature, reaction time, etc., are varied depending on the kinds of the reaction solvents used, the reaction starting materials and the oxidizing agents used. For instance, the reaction using m-chloroperbenzoic acid as the oxidizing agent and chloroform as the reaction solvent is carried out at the temperatures between −40° C. and 100° C., preferably −20° C. and 30° C. for the time between several minutes and several hours.

Representative examples of the compounds represented by formula (I) are recited below.
2-(2-Pyridylmethylsulfinyl)-quinoxaline,
2-(4-Quinolylmethylsulfinyl)-quinoxaline,
2-(2-Pyridylmethylsulfinyl)-3-(2-quinoxalyl)-quinoxaline,
2-(4-Quinolylmethylsulfinyl)-3-(2-quinoxalyl)-quinoxaline,
2-(2-Pyridylmethylthio)-quinoxaline,
2-(4-Quinolylmethylthio)-quinoxaline,
2-(2-Pyridylmethylthio)-3-(2-quinoxalyl)-quinoxaline, and
2-(4-Quinolylmethylthio)-3-(2-quinoxalyl)-quinoxaline.

The compounds of formula (I) can be converted, if desired, to pharmaceutically acceptable acid addition salts thereof which are included within the scope of the present invention.

Concrete examples of addition salts include the salts of the compounds with inorganic acids such as hydrochloric acid, hydrobromic acid, hydroiodic acid, nitric acid, sulfuric acid or phosphoric acid, and organic acids such as formic acid, acetic acid, propionic acid, butyric acid, maleic acid, fumaric acid, malonic acid, succinic acid, malic acid, citric acid, tartaric acid or oxalic acid.

The compounds of formula (I) and pharmaceutically acceptable acid addition salts thereof are of prominent antiulcer activity.

Thus, the present invention also provides antiulcer agents which comprise as an active ingredient the compounds of formula (I) or pharmaceutically acceptable acid addition salts thereof, optionally in admixture with additives for pharmaceutical preparation.

The pharmaceutical compositions of the invention may by formulated into various forms which are commonly used in the art and which are administered orally or parenterally. For example, they may be formulated into tablets, capsules, suppositories, troches, syrups, creams, ointments, granules, powders, injectable solutions or suspensions. Alternatively, they may be formulated into double or multiple layer tablets, together with other active principles. Furthermore, they may be formulated into coated tablets such as sugar-coated tablets, enteric-coated tablets and film-coated tablets.

In order to obtain solid preparations, the compound of this invention are mixed with such conventional diluents or fillers as lactose, refined sugar, crystalline cellulose, corn starch, calcium phosphate, sorbitol, glycine, carboxymethyl cellulose, gum arabic, polyvinylpyrrolidone, hydroxypropyl cellulose, glycerol, polyethylene glycol, stearic acid, magnesium stearate or talc.

In order to obtain semi-solid preparations, the compounds of this invention are mixed with such additives as plant wax, synthetic wax or fats.

In order to obtain liquid preparations, the compounds of this invention are mixed with such diluents or additives as sodium chloride, sorbitol, glycerol, olive oil, almond oil, propylene glycol or ethanol.

The compounds of the invention may normally be contained in a preparation in an amount of from 0.1 to 100% by weight, more suitably in an amount of from 1 to 50% by weight in the case of preparations for oral administration and from 0.2 to 20% by weight in the case of injectable preparations.

There is no particular limitation as to the method of administration and the dosage of the antiulcer agents according to the invention. They are chosen, depending on the form of preparation, age of patients, sex, degree of symptom, etc. Normally, however, the dosage will be in the range of from 10 to 1,000 mg per day.

The pharmaceutical composition of the invention may be administered in conjunction with one or more other active principles such as antacids, non-steroid anti-inflammatory agents or other types of antiulcer agents.

The invention is further illustrated by the following examples which are not to be construed to limit the scope thereof.

EXAMPLE 1

Preparation of 2-(2-pyridylmethylthio)-quinoxaline

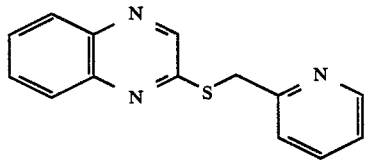

11.7 ml of 28% methanolic solution of sodium methoxide were added to a solution of 4.9 g of 2-mercaptoquinoxaline and 4.9 g of 2-chloromethylpyridine hydrochloride in 50 ml of methanol and stirred at room temperature for 5 hours.

The reaction solution was poured into 100 ml of water and extracted with chloroform. The chloroform layer was dried over sodium sulfate and evaporated under reduced pressure. The residue was purified by silica gel column chromatography eluting with 10% ethyl acetate/chloroform to give 4.51 g of the title compound.

Yellow crystals (from ether/hexane)
mp 64.8°–69.9° C.
NMR (CDCl$_3$) 4.73(2H,s), 7.10–7.20(1H,s), 7.49–7.75(4H,m), 7.87–8.04(2H,m), 8.06(1H,d, 5Hz), 8.12(1H,s)
IR (nujol): 1600, 1580
MASS: 253(M+), 220

EXAMPLE 2

Preparation of 2-(2-pyridylmethylthio)-3-(2-quinoxalyl)quinoxaline

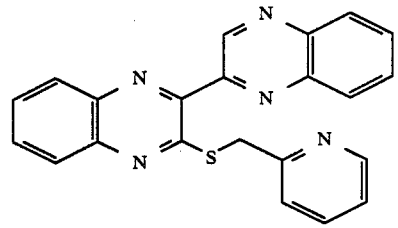

7.2 ml of 28% methanolic solution of sodium methoxide were added to a solution of 4.9 g of 2-mercapto-3-(2-quinoxalyl)-quinoxaline and 3.0 g of 2-chloromethylpyridine hydrochloride in 50 ml of methanol and stirred at room temperature for 5 hours.

The reaction solution was poured into 100 ml of water and extracted with chloroform. The chloroform layer was dried over sodium sulfate and evaporated under reduced pressure. The residue was purified by silica gel column chromatography eluting with 6% ethyl acetate/chloroform to give 1.62 g of the title compound.

Yellow crystals (from ethyl acetate)
mp 165.3°–167.5° C.
NMR (CDC13) 4.78(2H,s), 7.10–7.19(1H,m), 7.55–7.90 (6H,m), 8.00–8.07(1H,d,7Hz), 8.12–8.34(3H,m), 8.56(1H,d,5Hz), 9.97(1H,s)
IR (nujol): 1600, 1585
MASS: 381(M ), 348, 289

EXAMPLE 3

Preparation of 2-(4-quinolylmethylthio)-quinoxaline

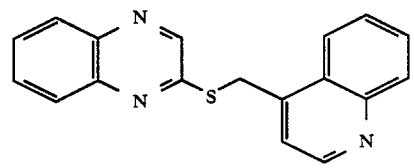

9.1 ml of 28% methanolic solution of sodium methoxide were added to a solution of 7.65 g of 2-mercaptoquinoxaline and 8.17 g of 4-chloromethylquinoline in 100 ml of methanol and stirred at room temperature for 4 hours.

To a reaction solution was added 100 ml of water, the solution was extracted with chloroform, and purified by silica gel column chromatography eluting with 10-15% ethyl acetate/chloroform to give 6.55 g of the title compound.

Yellow crystals (from isopropyl ether)
mp 94.1°-107.0° C.
NMR (CDCl3) 5.04(2H,s), 7.59-7.82(5H,m), 7.95-8.08 (2H,m), 8.21(2H,d,5Hz), 8.59(1H,s), 8.84(1H,d,5Hz)
IR (nujol): 1590
MASS: 303(M+), 270(100%), 173

EXAMPLE 4

Preparation of 2-(4-quinolylmethylthio)-3-(2-quinoxalyl)-quinoxaline

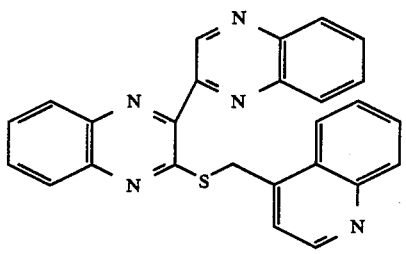

5.9 ml of 28% methanolic solution of sodium methoxide were added to a solution of 4.5 g of 2-mercapto-3-(2-quinoxalyl)-quinoxaline and 4.91 g of 4-chloromethylquinoline in 50 ml of methanol and stirred at room temperature for 5 hours.

The crystals precipitated in the reaction solution were collected by filtration. Recrystallization from chloroform/hexane gave 1.35 g of the title compound.

Yellow crystals (from chloroform/hexane)
mp (dec) 212.4°-214.2° C.
NMR (CDC13) 5.07(2H,s), 7.53-8.32(13H,m), 8.82(1H,d, 5Hz), 9.90(1H,s)
IR (nujol): 1600
MASS: 398(M+-33), 289

EXAMPLE 5

Preparation of 2-(2-pyridylmethylsulfinyl)-quinoxaline

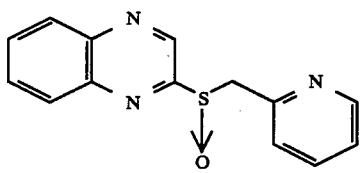

A solution of 1.2 g of 2-(2-pyridylmethylthio)quinoxaline and 1.0 g of m-chloroperbenzoic acid in 50 ml of chloroform was stirred for an hour under ice-water cooling.

The reaction solution was washed with an aqueous sodium carbonate solution, dried over sodium sulfate and evaporated under reduced pressure. The residue was purified by silica gel column chromatography eluting with ethyl acetate to give 1.08 g of the title compound.

White crystals (from ethyl acetate)
mp 124.8°-126.8° C.
NMR (CDCl13) 4.44(1H,d,13Hz), 4.69(1H,d,13Hz), 7.15-7.25(1H,m), 7.31(1H,d), 7.68(1H,t,8Hz), 7.81-7.92(2H,m), 8.08-8.24(2H,m), 8.39(1H,d,5Hz), 9.06(1H,s)
IR (nujol): 1590, 1050

EXAMPLE 6

Preparation of 2-(2-pyridylmethylsulfinyl)-3-(2-quinoxalyl)-quinoxaline

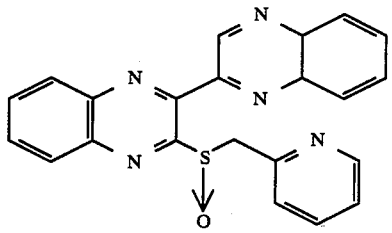

A solution of 0.63 g of 2-(2-pyridylmethylthio)-3-(2-quinoxalyl)-quinoxaline and 0.34 g of m-chloroperbenzoic acid in 50 ml of chloroform was stirred for one hour.

The reaction solution was washed with an aqueous sodium carbonate solution, dried over sodium sulfate and evaporated under reduced pressure. The residue was purified by silica gel column chromatography eluting with 50% acetone/chloroform to give 0.54 g of the title compound.

Yellow crystals (from chloroform/hexane)
mp (dec) 197.4° C.
NMR (CDCl3) 4.59(1H,d,12Hz), 5.22(1H,d,12Hz), 7.20-7.28(1H,m), 7.74(1H,t,7Hz), 7.04-8.01(4H,m), 8.20-8.27(1H,m), 8.31-8.43(2H,m), 8.54(1H,d,5Hz), 8.72-8.80(1H,m), 10.11(1H,s)
IR (nujol): 1610, 1590

EXAMPLE 7

Preparation of 2-(4-quinolylmethylsulfinyl)-quinoxaline

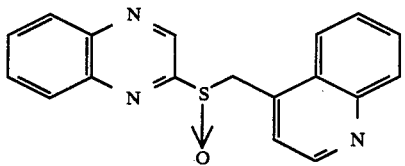

A solution of 6.5 g of 2-(4-quinolylmethylthio)-quinoxaline and 4.4 g of m-chloroperbenzoic acid in 100 ml of chloroform was stirred for one hour under ice-water cooling.

The reaction solution was washed with an aqueous sodium carbonate solution, dried over sodium sulfate and evaporated under reduced pressure. The residue was purified by silica gel column chromatography eluting with acetone to give 3.91 g of the title compound.

Pale yellow crystals (from ethyl acetate)
mp (dec) 147.1°-149.9° C.
NMR (CDCl3) 4.69(1H,d,13Hz), 4.96(1H,d,13Hz), 7.23-7.48(2H,m), 7.60(1H,t,8Hz), 7.79-7.95(3H,m), 8.03-8.18(3H,m), 8.83(1H,d,5Hz), 9.03(1H,s)
IR (nujol): 1600, 1060
MASS: 319(M30), 270, 142

EXAMPLE 8

Preparation of 2-(4-quinolylmethylsulfinyl)-3-(2-quinoxalyl)-quinoxaline

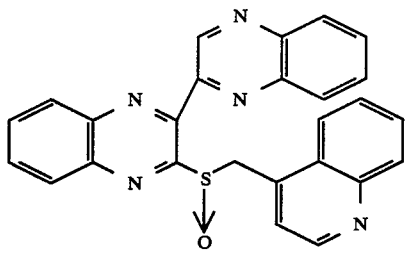

A solution of 1.1 g of 2-(4-quinolylmethylthio)-3(2-quinoxalyl)-quinoxaline and 0.75 g of m-chloroperbenzoic acid in 50 ml of chloroform was stirred for one hour under ice-water cooling.

The reaction solution was washed with an aqueous sodium carbonate solution, dried over sodium sulfate and evaporated under reduced pressure. The residue was purified by silica gel column chromatography eluting with acetone to give 0.41 g of the title compound.

Yellow crystals (from chloroform/hexane)
mp (dec) 182.2°–189.4° C.
NMR (CDC13) 5.04(1H,d,13Hz), 5.36(1H,d,13Hz), 7.12 (1H,t,8Hz), 7.42(1H,d,8Hz), 7.55(1H,d,4Hz), 7.64–8.28(10H,m), 8.90(1H,d,4Hz), 10.03(1H,s)
IR (nujol): 1590, 1050
MASS: 415($M^{30}$-32), 399, 397, 289, 144

EXAMPLE 9

This example illustrates the determination for the antiulcer activity of the compounds according to the invention.

Four-week-old ddY series male mice were used as the test animals after they were fasted for 24 hours. Each test compound suspended in a 1% gum arabic solution was administered to the stomach of each mouse at a dose of 100 mg/kg, and then, after 30 minutes, 20 mg/kg of indomethacin was administered orally. Four hours after the administration of indomethacin, the stomach of mouse was extirpated and the length of ulcers was measured. Then, the ulcer index was determined by the total sum of the scores as calculated in Table 1.

TABLE 1

| Length of ulcer | 0.5 mm< | 1 mm< | 2 mm< | 3 mm< |
|---|---|---|---|---|
| Score | 0.5 | 1 | 2 | 3 |

The mean ulcer index of each group was calculated and the suppression rate against the control group in terms of difference in the mean ulcer index was determined. The results are shown in Table 2.

TABLE 2

| Compound tested | Suppression rate of indomethacin induced ulcer, 100 mg/kg, p.o. |
|---|---|
| 2-(2-Pyridylmethylthio)-quinoxaline | 37 |
| 2-(4-Quinolylmethylsulfinyl)-quinoxaline | 61 |
| 2-(2-Pyridylmethylsulfinyl)-quinoxaline | 35 |

Table 2 shows that the compounds of the invention possess prominent antiulcer activity.

The following examples illustrate the various types of preparations which comprise as an active ingredient the compounds of the invention.

Preparation 1: Tablet 50 mg of 2-(4-quinolylmethylsulfinyl)-quinoxaline, 77 mg of lactose, 15 mg of crystalline cellulose, 7 mg of corn starch and 1 mg of magnesium stearate (each per tablet) were thoroughly mixed, and then the mixture was tableted with a rotary tableting machine into a tablet of 7 mm diameter, weight 150 mg.

Preparation 2: Granule 50 mg of 2-(4-quinolylmethylsulfinyl)-quinoxaline, 230 mg of lactose, 110 mg of corn starch and 100 mg of crystalline cellulose were thoroughly mixed. Meanwhile, 10 mg of hydroxypropyl cellulose were dissolved in 90 mg of ethanol and the solution was added to the previously prepared mixture. The whole mixture was kneaded and granulated. The granules were air-dried at 50° C. and then sieved into the grain size of from 297 μm to 1460 μm. 500 mg of the granules were packed into a unit dosage form.

Preparation 3: Syrup 5 g of 2-(4-quinolylmethylsulfinyl)-quinoxaline, 30 g of refined sugar, 25 g of 70 w/v % D-sorbitol, 0.03 g of ethyl p-hydroxybenzoate and 0.015 g of propyl p-hydroxybenzoate were dissolved in 60 ml of warmed water. After the solution was cooled, a solution of 0.2 g of a flavor in 0.15 g of glycerol and 0.5 g of 96% ethanol was added. The whole mixture was diluted with water to balance 100 ml.

Preparation 4: Injectable solution 5 mg of 2-(2-pyridylmethylthio)-quinoxaline and 10 mg of sodium chloride were dissolved in sterilized distilled water to balance 1 ml.

Preparation 5: Suppository 20 g of polyethylene glycol 4000 were added to a solution of 10 g of 2-(4-quinolylmethylsulfinyl)-quinoxaline in 70 g of glycerol. The mixture was warmed and poured into a suppository mold and then cooled to give suppositories, each weighing 1.5 g.

What is claimed is:

1. A compound of formula (I)

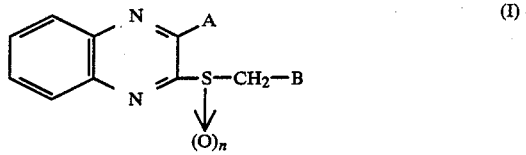

wherein A is a hydrogen atom or 2-quinoxalyl, B is 2-pyridyl or 4-quinolyl and n is 0 or 1, excluding the case where A is a hydrogen atom and B is 2-pyridyl or a pharmaceutically acceptable acid addition salt thereof.

2. A compound of claim 1, wherein A is a hydrogen atom, B is 4-quinolyl and n is 0.

3. A compound of claim 1 wherein A is 2-quinoxalyl, B is 2-pyridyl or 4-quinolyl and n is 0.

4. A compound of claim 1 wherein A is a hydrogen atom, B is 4-quinolyl and n is 1.

5. A compound of claim 1 wherein A is 2-quinoxalyl, B is 2-pyridyl or 4-quinolyl and n is 1.

6. An antiulcer agent which comprises as an active ingredient a therapeutically effective amount of a compound of formula (I).

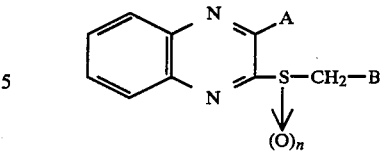

wherein A is a hydrogen atom or 2-quinoxalyl, B is 2-pyridyl or 4-quinolyl and n is 0 or 1, excluding the case where A is a hydrogen atom and B is 2-pyridyl, or a pharmaceutically acceptable acid addition salt thereof, and a pharmaceutically acceptable carrier.

7. An antiulcer agent of claim 6 wherein the active ingredient is a compound of formula (I) wherein A is a hydrogen atom, B is 4-quinolyl and n is 0 or 1, or a pharmaceutically acceptable acid addition salt thereof, and a pharmaceutically acceptable carrier.

* * * * *